(12) United States Patent
Price

(10) Patent No.: US 6,676,591 B2
(45) Date of Patent: Jan. 13, 2004

(54) MAGNOTHERAPY DEVICE AND USE THEREOF

(75) Inventor: Derek Raymond Price, Bristol (GB)

(73) Assignee: Magno-Pulse Limited, Bristol (GB)

( * ) Notice: Subject to any disclaimer, the term of this patent is extended or adjusted under 35 U.S.C. 154(b) by 0 days.

(21) Appl. No.: 10/119,329

(22) Filed: Apr. 9, 2002

(65) Prior Publication Data

US 2002/0183583 A1 Dec. 5, 2002

(30) Foreign Application Priority Data

Apr. 10, 2001 (GB) .............................. 108964
Jan. 24, 2002 (GB) .............................. 201623

(51) Int. Cl.⁷ ............................ A61B 17/52; A61N 2/00
(52) U.S. Cl. ...................................................... 600/9
(58) Field of Search .................. 600/9, 15; 24/303, 24/356, 709.2

(56) References Cited

U.S. PATENT DOCUMENTS 5,732,451 A * 3/1998 Mars .......................... 24/303
5,782,743 A * 7/1998 Russell ........................ 600/9
5,827,170 A * 10/1998 Gebran ....................... 600/15
6,146,324 A * 11/2000 Engel ......................... 600/15

FOREIGN PATENT DOCUMENTS

| GB | 2307178 A | 5/1997 |
| JP | 9-248345 A | 9/1997 |
| JP | 10-225497 A | 8/1998 |
| JP | 11-056963 A | 3/1999 |
| JP | 11-350212 A | 12/1999 |

* cited by examiner

Primary Examiner—Max F. Hindenburg
Assistant Examiner—Brian Szmal
(74) Attorney, Agent, or Firm—Reising, Ethington, Barnes, Kisselle, P.C.

(57) ABSTRACT

A magnotherapy device is provided which contains a magnet within an enclosure. The device is associated with a further magnetic attachment means 32 which is itself attracted to the magnotherapy device such that an item of clothing can be clamped between the magnotherapy device and the attachment means.

11 Claims, 2 Drawing Sheets

MAGNOTHERAPY DEVICE AND USE THEREOF

BACKGROUND TO THE INVENTION

The present invention relates to a magnotherapy device for use in magnotherapy, especially but not exclusively as practised on the human body.

Magnotherapy describes the practise of placing magnets adjacent an animal or human body in order to cure a disease, alleviate symptoms or enhance performance of the animal/human.

The mechanism by which magnotherapy works is not well understood. However the fact that it works on animus as well as humans suggests that there is a physical interaction between the magnetic field and the body, and that the results are not psychosomatic. A discussion of magnotherapy can be found in the book "Magnetic Health, Modern Day. Healing with Magnets" by D R Price (ISN0953679705). It is believed that the application of a magnetic field restores the efficiency of the blood stream, and that the improvement in circulation helps the body repair itself more efficiently resulting in improvements in the skin conditions, improvements in the cosmetic appearance of the skin, and improvements in conditions including cramp, angina, local aches and pains, arthritis, migraine, ME, MS and gout.

It is known that sexual dysfunction for example impotence in males, can be effected by, circulatory problems. The media attention surrounding the launch of VIAGRA. (registered trade mark) demonstrated that a large proportion of the population had interest in improving their sexual performance. A "black market" for the drug became apparent with instances of its use by those who were not clinically impotent. In the UK, the drug remains available only on prescription due to its side effects such as increased blood pressure. Furthermore the embarrassment factor of a patient having to visit his doctor in order to obtain the drug on prescription may prevent some sufferers of impotence who could exhibit a clinical improvement as a result of using the drug from failing to obtain it. IT is believed that magnotherapy can help sufferers of impotence.

The applicant has conducted confidential trials which indicate that magnotherapy also provides relief from period pains.

To date, there has been no report of side effects with the use of magnotherapy.

Magnotherapy practitioners have developed a terminology in which one pole of the magnet is described as positive and the other pole of the magnet is described as negative. This convention will be used throughout the specification, although it differs from the terminology convention used referring to magnets having north poles and south poles. The terms positive and negative as used herein are defined as follows:

For a freely moveable magnet the "negative" pole is the pole which is attracted towards the geographic South Pole of the earth, and correspondingly the "positive" pole is the pole attracted to the geographical North Pole.

DESCRIPTION OF THE INVENTION

According to the first aspect of the present invention, there is provided a magnotherapy product comprising a magnet having positive and negative poles, said magnet being held in a housing having magnetic attachment means for attachment to an article of clothing.

It is thus possible to provide a magnotherapy product which can be easily attached to an article of clothing worn by a user. This has the advantage that the product can be easily and discretely worn near to a region where the benefits of therapy are required.

Preferably a first side of the product is adapted, in uses to face the flesh of a wearer. Advantageously the negative pole of a magnet is arranged, in use, to face the flesh of the wearer.

The magnet may be encapsulated within a housing. The housing may protect the surface of the magnet from damage due to moisture, dust or physical contact. In an embodiment of the present invention, a magnet is enclosed between two half shells of a housing, the housing and magnet being glued together by a hot melt adhesive such that the space inside the housing is substantially filled and the magnet is totally enclosed.

In an alternative embodiment the casing may be composed of a three dimensional ease into which a magnet is placed and which is closed by a planar element. The casing may be profiled so as to indicate which side of the device should be placed facing the user's skin.

Preferably a metallic plate is provided adjacent the positive pole of the magnet. The plate is preferably non-ferromagnetic. The plate may, for example be made of stainless steel. The plate advantageously covers the entirety of the positive pole and acts to alter the magnetic field around the positive pole so as to attenuate the magnetic field strength above and adjacent the plate. This serves to reduce the tendency of the magnet to attract magnetic material in the vicinity of the user. The presence of the plate also distorts the magnetic field in the vicinity of the negative pole such that the field strength near the negative pole is increased and consequently the field propagates further into the body of a user.

In initial confidential trials, magnotherapy devices had been provided with resilient clips in order to attach to a wearer's clothing. However, clips necessarily need to be placed over the edge of a garment or need to gather folds of the garment within the clip in order to attach.

Preferably the attachment to a user's clothing is performed using magnetic attachment means. The magnotherapy device exhibits a magnetic field on the side facing away from the user's flesh. This field, even though of reduced strength, is sufficient to attract metallic element such that a user's clothes can be clamped between the magnotherapy device and the metallic element Preferably a further magnet is provided in a separate magnetic attachment means. The further magnet may be provided in an encapsulated form, such as in a plastic case. The further magnet is attracted to the plate. Furthermore the case of the magnotherapy device may be profiled to define a centering region such that the position of the separate attachment means when magnetically attracted to the magnotherapy device is well defined.

In a preferred embodiment of the present invention the magnet in the body of the magnotherapy device is the same size as the magnet in the magnetic attachment means, i.e. same diameter. Furthermore, the metallic plate is positioned against or adjacent the magnet in the attachment means on the side which, in use, faces away from the user. Thus the position of the attachment means with respect to the magnotherapy device is well defined.

It will be appreciated that other attachment methods may also be employed. Thus a surface of the housing may be provided with a plurality of hooks or a plurality of eyes thereon, for inter-engaging with a clip or a belt worn by the user. A hook and eye fastening method is commercially available under the trade mark Velcro. Thus the product may be positioned adjacent other parts of the body in order to provide local relief As a further alternative, a clip may be provided as a resilient element having a portion which runs adjacent a surface of the housing such that an item of clothing can be engaged between the portion of the clip and the housing so as to hold the magnotherapy device attached to the item of clothing.

According to a second aspect of the present invention there is provided an undergarment having at least one engagement means for engaging a magnet so as to hold the magnet adjacent the surface of a wearers body at a predetermined position.

Advantageously the predetermined position is adjacent the femoral artery. Alternatively the predetermined position is adjacent the wearer's genitalia. The engagement means may be a pocket.

According to a third aspect of the present invention there is provided a method of treatment of impotence, comprising placing a negative pole of a magnet adjacent a user's flesh in the vicinity of one of the penis and the femoral artery.

According to a fourth aspect of the present invention there is provided a method of cosmetic treatment of the appearance of the penis when erect, the method comprising the placement of a negative pole of a magnet adjacent the user's flesh in the vicinity of one of the penis and the femoral artery in order that improved blood flow to the penis creates a more cosmetically pleasing erection.

According to a fifth aspect of the present invention there is provided the use of a magnet in the manufacture of a therapeutic device for the treatment of impotence.

According to a sixth aspect of the present invention, there is provided a method of reducing or alleviating period pains, the method comprising placing the negative pole of magnet adjacent the user's flesh in the vicinity of an artery.

It has been noted, in confidential trials of the device, that female users found relief during their periods when wearing the device. This is believed to be a consequence of improved blood circulation.

Preferably the magnet is placed adjacent the femoral artery.

BRIEF DESCRIPTION OF THE ACCOMPANYING DRAWINGS

The present invention will further be described, by way of example, with reference to the accompanying drawings, in which.

DESCRIPTION OF EMBODIMENTS OF THE INVENTION

Figure 1:
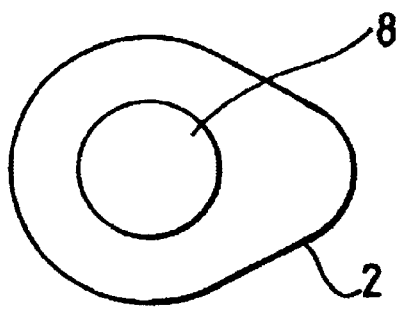
FIG. 1 is a plan section through a magnotherapy device constituting an embodiment of the present invention.
Figure 2:
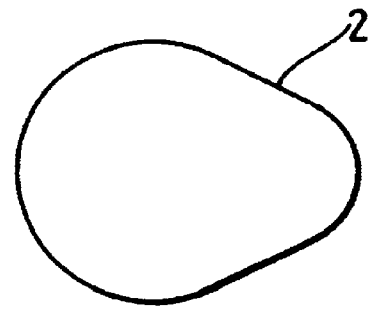
FIG. 2 is a view of a first face of the device shown in FIG. 1.
Figure 3:
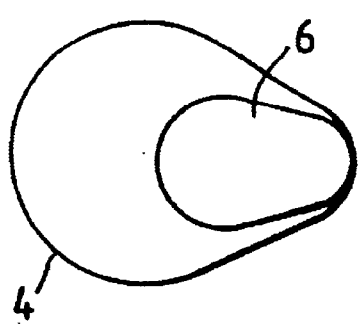
FIG. 3 is a view of a second face of the device.
Figure 4:
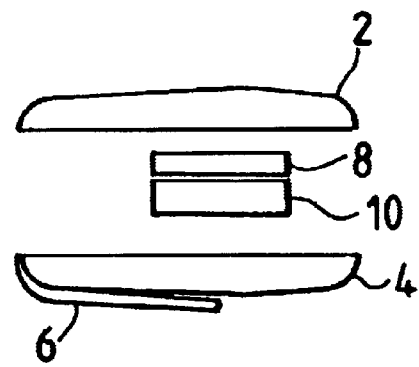
FIG. 4 is an expanded view of the device with its housing separated in order to reveal the internal components.
Figure 5:
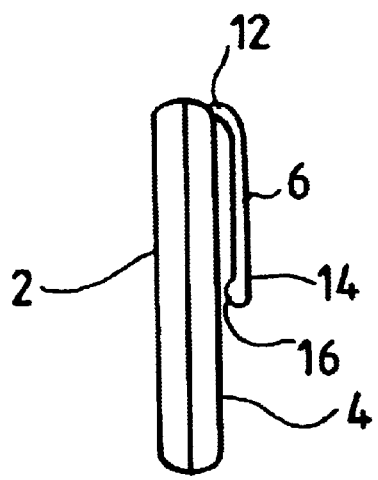
FIG. 5 is a side view of the device.

The device shown in the accompanying FIGS. 1 to 5 comprises a body formed by a first half shell 2 which co-operates with a second half shell 4 in order to define a volume internal to the shells for holding a magnet 8 and a cover element 10.

The magnet is a single disc shaped rare earth magnet alloy, such as ncodymium iron boron as these magnets give high magnetic flux for low physical volume. The magnet is positioned such that its negative pole is adjacent or in contact with the innermost surface of the first shell 2. The positive pole of the magnet is spaced apart from the inner race of the second shell 4 by the element 10 which is formed of a disc of non-magnetic metal, such as stainless steel. The shells 2 and 4 are bonded together so as to encapsulate the magnet 8 and element 10 inside the housing. For convenience adhesive is used in a hot melt process such that the void within the housing is completely filled by adhesive, thereby preventing any rattling of the magnet 8 or element 10 within the housing. Furthermore the magnet is sealed from moisture.

A resilient clip 6 extends from the second side of the housing 4 in order that an item of clothing can be entrained between the clip 6 and the housing 4 in order to attach the device to the clothing. The clip 6 has a fixed end 12 which is attached to the housing FIG. 5) and a free end 14 which advantageously carries a projection 16 thereon in order to further enhance the gripping action of the grip 6.

In use, the device can be clipped onto the wearer's underpants with the housing being held between the underpants and the user's flesh such that the first side 2 faces towards the body thereby presenting the negative pole of the magnet to the body. The device is positioned by the user towards the front of the underpants, but displaced to one side so as to position the device adjacent the femoral artery.

Figure 6:
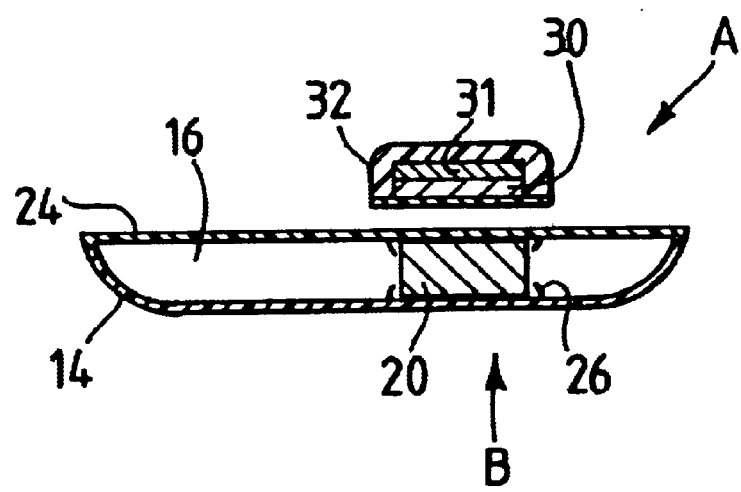
FIG. 6 is a cross section though a device constituting a further embodiment of the present invention.

FIG. 6 shows an alternative embodiment of the present invention which is in many ways similar to those described hereinbefore, except in respect of the fixing device. A moulded plastic shell 14 defines a cavity 16 in which a magnet 20 is disposed. An end wall 24 is provided to seal the case 14. The end wall and the case 14 have upstanding projections 20 formed thereon in order to locate the magnet 20 at it's correct position. A further magnet 30 encapsulated inside its own plastic housing 32 is provided to act as an attachment element. The magnet 30 is in association with a steel plate 31.

In a preferred embodiment, the magnet 20 is 5 mm thick and 20 mm in diameter and has a magnetic strength of 2300 gauss on each face thereof. The magnet 30 is 1 mm thick by 20 mm in diameter and the steel plate 31 is 2 mm thick by 20 mm in diameter and is formed of 430 grade stainless steel.

As noted hereinbefore the effect of the steel plate 31 is to distort the magnetic field such that it be comes decreased on the side, labelled A, which faces away from the user's body and becomes increased on the side B which faces towards the user's body. The following table shows that by including the stainless steel plate the magnetic field at a distance between 10 and 20 mm from the surface of the magnotherapy device is increased by approximately 60%.

| Distance from surface (mm) | Magnetic Field Reading (Gauss) side with steel plate - Side A | Magnetic Field Reading (Gauss) side without steel plate - Side B |
| --- | --- | --- |
|  | 790 | 2700 |
| 5 | 530 | 1290 |
| 10 | 300 | 500 |
| 15 | 180 | 280 |

-continued

| Distance from surface (mm) | Magnetic Field Reading (Gauss) side with steel plate - Side A | Magnetic Field Reading (Gauss) side without steel plate - Side B |
| --- | --- | --- |
| 20 | 100 | 160 |
| 30 | 50 | 70 |
| 40 | 20 | 32 |
| 50 | 15 | 20 |
| 60 | 5 | 10 |
| 70 | 0 | 5 |

A user such as a women seeking relief from period pain, places the magnotherapy device in a position such that it lies directly over the uterus and next to the skin with the curved surface, labelled B, facing towards the skin. For ease, the magnotherapy device is placed inside the underpants, and the attachment element comprising the magnet 30 plate 31 is placed outside the underpants and adjacent the magnotherapy device such that the magnet 30 is attracted to the magnet 20 thereby clamping the undergarment between the magnotherapy device and the attachment element. This ensures that the magnotherapy device is held in the correct position, without damaging the user's clothing. The feature of having the magnets facing each other ensures a good clamping action and ensures that the relative positions of the magnet are well defined. The steel plate 31 faces away from the user but still provides the desired modification of the magnetic field distribution.

It is thus possible to provide a magnotherapy device which presents only a single pole towards the human body and which can be used for the treatment of menstrual pain.

What is claimed is:

1. A magnotherapy product comprising a magnet having positive and negative poles, said magnet being held in a housing which has attachment means for attachment to an article of clothing, and wherein a metallic element is provided adjacent the positive pole of the magnet, and a surface thereof facing the positive pole is substantially the same size as the positive pole so as to cover it, whereby the metallic element distorts the magnetic field distribution around the magnet so as to attenuate the magnetic field in the vicinity of the positive role of the magnet.

2. A magnotherapy product as claimed in claim 1, in which, in use, the negative pole of the magnet faces the flesh of a user.

3. A magnotherapy product as claimed in claim 1, in which the magnet is encapsulated within the housing.

4. A magnotherapy product as claimed in claim 1, in which the housing comprises first and second shells co-operating to define a volume for containing the magnet.

5. A magnotherapy product as claimed in claim 4, in which the space inside the housing is filled with an adhesive.

6. A magnotherapy device as claimed in claim 1, in which the element is a plate.

7. A magnotherapy device as claimed in claim 1, in which the element distorts the magnetic field around the magnet so as to increase the magnetic field strength in the vicinity of the negative pole.

8. A magnotherapy device as claimed in claim 1, in which the attachment means is a clip is attached at a first end thereof to the housing and which has a free second end which co-operates with the housing to engage an item of clothing therebetween.

9. A magnotherapy device as claimed in claim 1, in which the attachment means comprises co-operating hooks and eyes to engage the product with an item of clothing.

10. A magnotherapy device as claimed in claim 1, in which the attachment means comprises a magnetic element which is attracted to the magnotherapy device in order to clamp an item of clothing, the attachment means comprises a magnet, the metallic plate is adjacent the magnet of the attachment means, and the magnet of the attachment means, the magnetic element and the magnet are the same diameter.

11. An undergarment having at least one engagement means for engaging with a magnet so as to hold the magnet adjacent the surface of a wearer's body at a predetermined position, wherein a negative pole of the magnet faces towards the user, a positive pole of the magnet faces away from the user, and a plate overlies the positive pole in a non-overhanging manner so as to attenuate the magnetic field in the vicinity of the positive pole and to increase the magnetic field strength in the vicinity of the negative pole.

* * * * *